US012608033B2

(12) United States Patent
Kimura et al.

(10) Patent No.: US 12,608,033 B2
(45) Date of Patent: Apr. 21, 2026

(54) PUSH BUTTON DEVICE FOR ENDOSCOPE, AND ENDOSCOPE

(71) Applicants:OLYMPUS CORPORATION, Tokyo (JP); ALPS ALPINE CO., LTD., Tokyo (JP)

(72) Inventors: Shunsuke Kimura, Aizuwakamatsu (JP); Reiji Koyama, Kawagoe (JP); Tetsu Numata, Miyagi (JP); Shigeto Gorai, Miyagi (JP); Akihiro Kusaka, Miyagi (JP)

(73) Assignees: OLYMPUS CORPORATION, Tokyo (JP); ALPS ALPINE CO., LTD., Tokyo (JP)

( * ) Notice: Subject to any disclaimer, the term of this patent is extended or adjusted under 35 U.S.C. 154(b) by 479 days.

(21) Appl. No.: 17/724,740

(22) Filed: Apr. 20, 2022

(65) Prior Publication Data

US 2022/0244751 A1     Aug. 4, 2022

Related U.S. Application Data

(63) Continuation of application No. PCT/JP2020/039679, filed on Oct. 22, 2020.

(30) Foreign Application Priority Data

Oct. 29, 2019     (JP) ................................. 2019-196703

(51) Int. Cl.
 *G05G 1/02* (2006.01)
 *A61B 1/00* (2006.01)
 *G02B 23/24* (2006.01)
(52) U.S. Cl.
 CPC ........... *G05G 1/02* (2013.01); *G02B 23/2476* (2013.01); *A61B 1/00042* (2022.02)

(58) Field of Classification Search
 CPC .. G05G 1/02; G02B 23/2476; A61B 1/00042; A61B 1/00066; A61B 1/00068;
 (Continued)

(56) References Cited

U.S. PATENT DOCUMENTS

| | | |
|---|---|---|
| 4,617,915 A | 10/1986 | Arakawa |
| 4,845,555 A | 7/1989 | Yabe et al. |
| 2004/0060718 A1 | 4/2004 | Izumisawa |

FOREIGN PATENT DOCUMENTS

| | | |
|---|---|---|
| JP | S63-197430 A | 8/1988 |
| JP | S64-018547 U | 1/1989 |
| | (Continued) | |

OTHER PUBLICATIONS

International Search Report Dated Dec. 22, 2020 received in PCT/JP2020/039679.

(Continued)

*Primary Examiner* — Michael J Carey
*Assistant Examiner* — Timothy Tuan Luu
(74) *Attorney, Agent, or Firm* — Sculy, Scott, Murphy & Presser, P.C.

(57)     ABSTRACT

A push button device for an endoscope includes: a connection member having a bottomed tubular shape and provided to a finger placement member, the finger placement member having elasticity and disposed on an exterior member of the endoscope; a first stem that has an upper end portion inserted and fitted into the connection member and that is slidably and swingably disposed; a second stem slidably and swingably provided and configured to move in conjunction with motion of the first stem; an immobile member slidably and swingably holding the first stem and the second stem; and a switch configured to be switched by displacement of the second stem moving in conjunction with the motion of the first stem when the finger placement member is pushed.

19 Claims, 6 Drawing Sheets

(58) Field of Classification Search
CPC .. A61B 1/00039; A61B 1/0004; H01H 21/00;
H01H 21/22
See application file for complete search history.

(56) References Cited

FOREIGN PATENT DOCUMENTS

| | | | |
|----|-------------------|------|---------|
| JP | H02-135002 A | | 5/1990 |
| JP | 105-211987 A | | 8/1993 |
| JP | H05211987 A | * | 8/1993 |
| JP | H09-173278 A | | 7/1997 |
| JP | 2000-201882 A | | 7/2000 |
| JP | 2000287917 A | | 10/2000 |
| JP | 3181657 B2 | | 7/2001 |
| JP | 2002-190228 A | | 7/2002 |
| JP | 2010142255 A | * | 7/2010 |
| JP | 2010-272322 A | | 12/2010 |
| JP | 2014-117574 A | | 6/2014 |
| JP | 2018134354 A | * | 8/2018 |
| JP | 2019-041885 A | | 3/2019 |
| JP | 2019-175543 A | | 10/2019 |
| WO | WO-2017082204 A1 | * | 5/2017 ............... A61B 1/00 |
| WO | 2021/085289 A1 | | 5/2021 |

OTHER PUBLICATIONS

US Office Action dated Feb. 27, 2025 received in U.S. Appl. No. 17/725,891.
US Office Action dated Aug. 15, 2024 issued in U.S. Appl. No. 17/725,891.

* cited by examiner

PUSH BUTTON DEVICE FOR ENDOSCOPE, AND ENDOSCOPE

CROSS REFERENCE TO RELATED APPLICATION

This application is a continuation application of PCT/JP2020/039679 filed on Oct. 22, 2020 and claims benefit of Japanese Application No. 2019-196703 filed in Japan on Oct. 29, 2019, the entire contents of which are incorporated herein by this reference.

BACKGROUND OF THE INVENTION

1. Field of the Invention

The present invention relates to a push button device for an endoscope, the push button device being provided on an operation portion or the like, and to an endoscope.

2. Description of the Related Art

As is well known, an endoscope is widely used for observation, treatment, and the like inside a living body (inside a body cavity), and for examination, repair, and the like inside an industrial plant facility. Such an endoscope includes an operation portion that is grasped by a user, and the operation portion is provided with, for example, a bending operation knob for performing bending operation of a bending portion provided in an insertion portion, and a push button for operating an external instrument such as a light source device or a video processor.

For example, a push button device for an endoscope as disclosed in Japanese Patent Application Laid-Open Publication No. 5-211987 is well known as such a push button provided on an endoscope. The push button device of an operation portion for an endoscope according to Japanese Patent Application Laid-Open Publication No. 5-211987 is disclosed as a technology for a structure that includes a finger placement portion protruding from an exterior case and with which a switch is actuated even when the finger placement portion is pushed in a side direction or an oblique direction.

SUMMARY OF THE INVENTION

A push button device for an endoscope according to an aspect of the present invention includes: a finger placement member having elasticity and disposed at an operation portion of the endoscope; a connection member having a bottomed tubular shape and provided at the finger placement member; a first stem that has an upper end portion inserted and fitted into the connection member, the first stem being disposed so as to be slidable along a longitudinal axis and swingable; a second stem provided so as to be slidable along the longitudinal axis and swingable, and configured to move in conjunction with motion of the first stem with an upper end surface being in contact with a lower end surface of the first stem; an immobile member slidably and swingably holding the first stem and the second stem; and a switch configured to be switched by displacement of the second stem moving in conjunction with the motion of the first stem when the finger placement member is pushed.

An endoscope according to an aspect of the present invention includes: an operation portion that is grasped by a user; a finger placement member having elasticity and disposed at the operation portion; a connection member having a bottomed tubular shape and provided at the finger placement member; a first stem that has an upper end portion inserted and fitted into the connection member, the first stem being disposed so as to be slidable along a longitudinal axis and swingable; a second stem provided so as to be slidable along the longitudinal axis and swingable, and configured to move in conjunction with motion of the first stem with an upper end surface being in contact with a lower end surface of the first stem; an immobile member slidably and swingably holding the first stem and the second stem; and a switch configured to be switched by displacement of the second stem moving in conjunction with the motion of the first stem when the finger placement member is pushed.

DETAILED DESCRIPTION OF THE PREFERRED EMBODIMENT

The following description will be made with an example of an endoscope including a push button mechanism of the present invention. Note that, in the following description, drawings based on each embodiment are schematic, and relations between thicknesses and widths of each part, thickness ratios of respective parts, and the like may be different from actual ones. Dimensional relations between elements and ratios of elements may also differ between the drawings in some cases.

An endoscope in the following configuration explanation will be described with an example of what is called a flexible endoscope in which an insertion portion has flexibility for insertion into a digestive system in an upper portion or a lower portion of a living body, but is not limited to a flexible endoscope and is a technology that is also applicable to what is called a rigid endoscope that includes a rigid insertion portion and is used for surgery, and an industrial endoscope for examining an engine, a plant, or the like.

A push button mechanism for an endoscope according to an aspect of the present invention will be described below with reference to the accompanying drawings.

Figure 1:
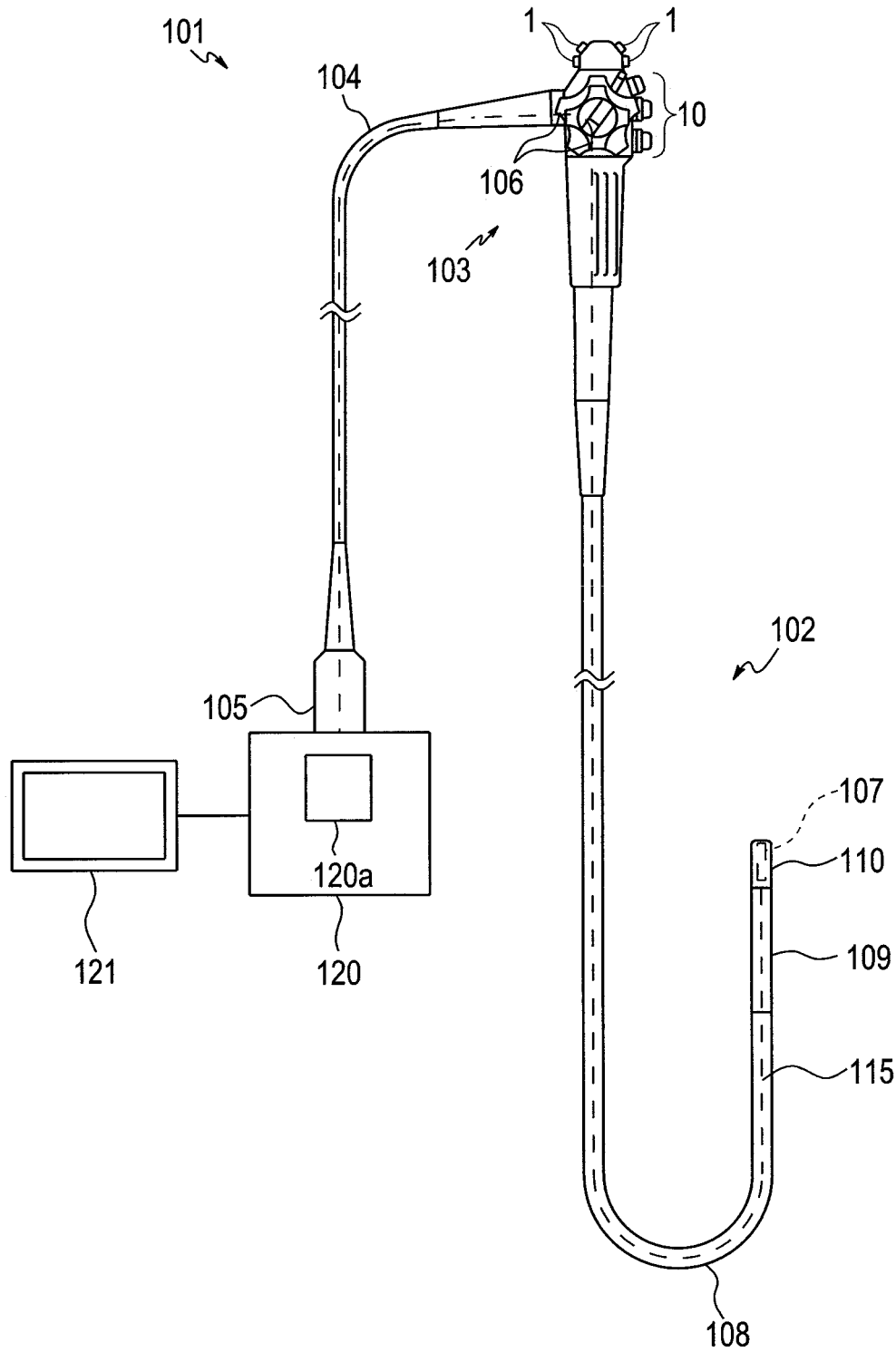
FIG. 1 is a diagram illustrating an appearance of an endoscope in which a push button mechanism according to an aspect of the present invention is provided at an operation portion.
Figure 2:
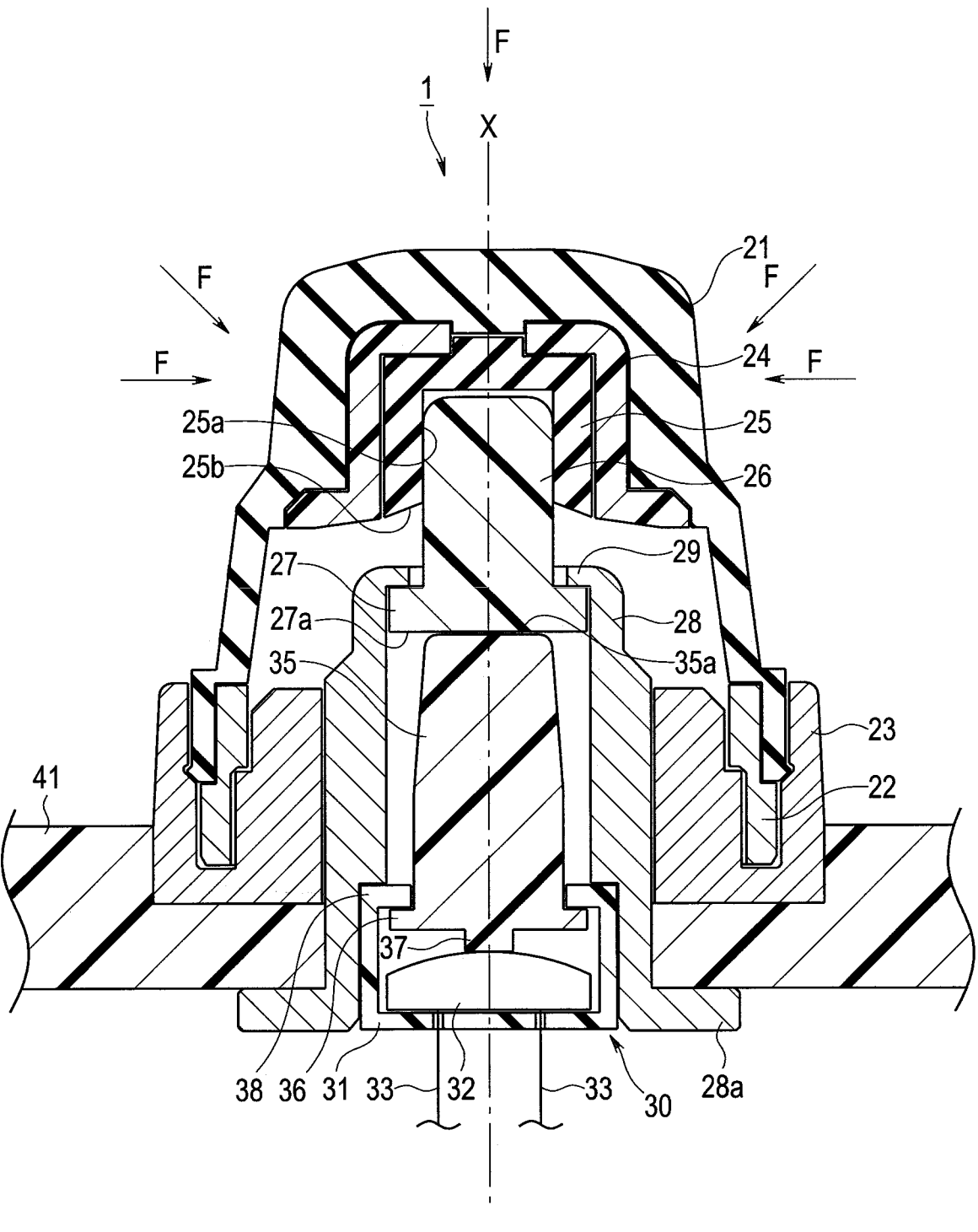
FIG. 2 is a cross-sectional view illustrating a configuration of a push button unit.
Figure 3:
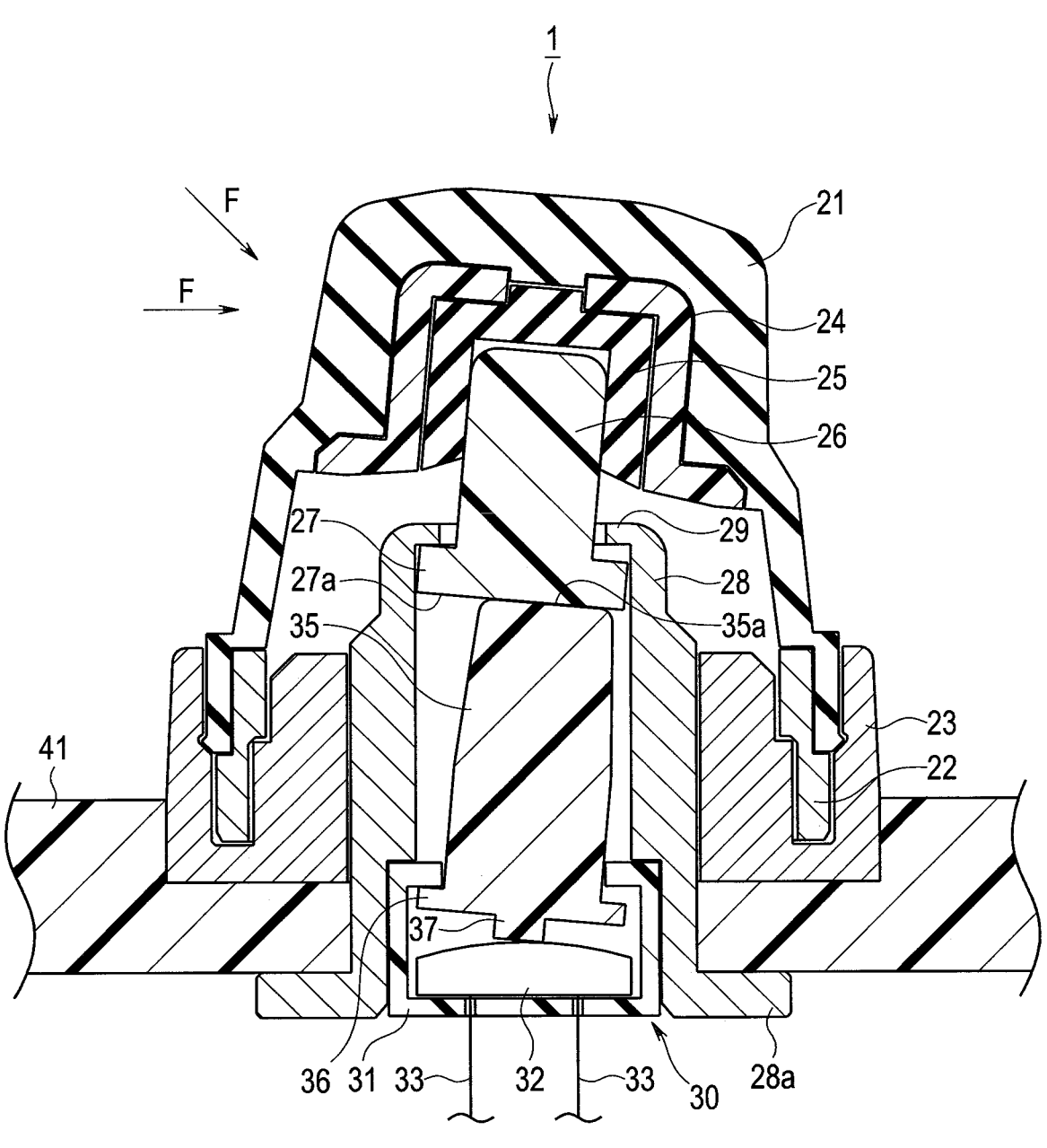
FIG. 3 is a cross-sectional view illustrating a configuration of the push button unit in a state of being pushed in a side direction or an oblique direction.
Figure 4:
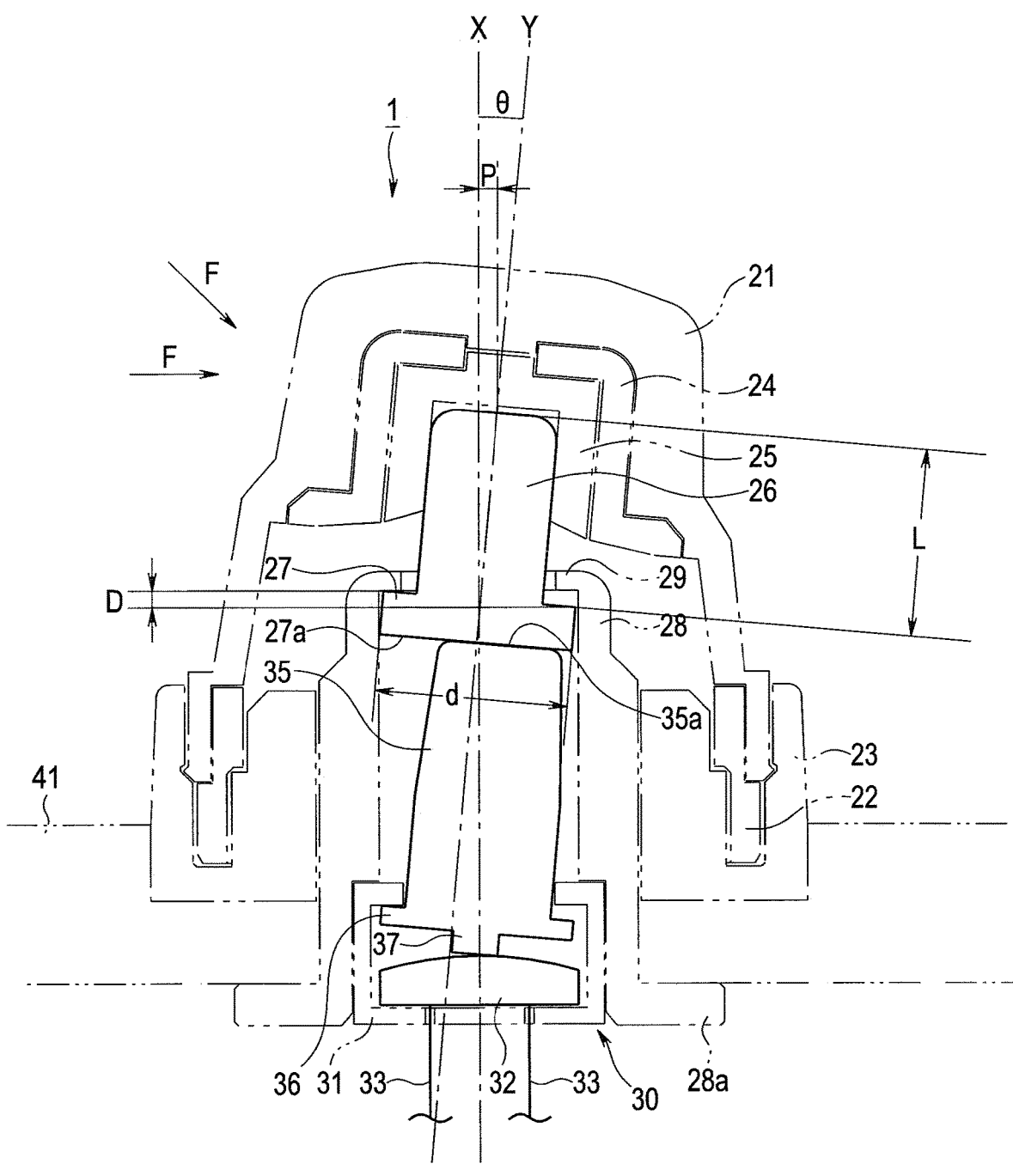
FIG. 4 is a diagram illustrating a state in which a rubber cap is pushed in a side direction or an oblique direction, indicating a relation among a tilt angle, a length, and the like of a first stem of the push button unit.

FIG. 1 is a diagram illustrating an appearance of an endoscope in which the push button mechanism according to the aspect of the present invention is provided at an operation portion, FIG. 2 is a cross-sectional view illustrating a configuration of a push button unit, FIG. 3 is a cross-sectional view illustrating a configuration of the push button unit in a state of being pushed in a side direction or an oblique direction, and FIG. 4 is a diagram illustrating a state in which a rubber cap is pushed in a side direction or an oblique direction, indicating a relation among a tilt angle, a length, and the like of a first stem of the push button unit.

First, an example of a configuration of an endoscope 101 in which a push button unit 1 as a push button mechanism for an endoscope according to the present invention is provided at an operation portion 103 will be described with reference to FIG. 1.

The endoscope 101 of the present embodiment can be introduced into a subject such as a human body and is configured to optically pick up an image of a predetermined observation site in the subject.

Note that the subject into which the endoscope 101 is introduced is not limited to a human body but may be any other living body or may be an artificial object such as a machine or a building.

The endoscope 101 mainly includes an insertion portion 102 that is introduced into the subject, the operation portion 103 positioned at a proximal end of the insertion portion 102, and a universal cord 104 extending from a side part of the operation portion 103.

The insertion portion 102 has a configuration in which a distal end portion 110, a bending portion 109, and a flexible tube portion 108 are continuously provided, the distal end portion 110 being disposed at a distal end, the bending portion 109 being bendable and disposed on a proximal end side of the distal end portion 110, the flexible tube portion 108 having flexibility, disposed on the proximal end side of the bending portion 109, and connected to the distal end side of the operation portion 103.

An image pickup unit 107 is provided at the distal end portion 110. An angle operation knob 106 for operating bending of the bending portion 109 is provided at the operation portion 103.

An endoscope connector 105 that is connected to an external device 120 is provided at a proximal end portion of the universal cord 104. The external device 120 connected to the endoscope connector 105 is connected to an image display unit 121 such as a monitor through a cable.

The endoscope 101 also includes a composite cable 115 (not illustrated) inserted in the universal cord 104, the operation portion 103, and the insertion portion 102, and includes an optical fiber bundle (not illustrated in the drawing) that transmits illumination light from a light source unit provided at the external device 120.

The composite cable 115 is configured to electrically connect the endoscope connector 105 and the image pickup unit 107. When the endoscope connector 105 is connected to the external device 120, the image pickup unit 107 is electrically connected to the external device 120 through the composite cable 115.

Electric power supply from the external device 120 to the image pickup unit 107 and communication between the external device 120 and the image pickup unit 107 are performed through the composite cable 115.

An image processing unit is provided at the external device 120. The image processing unit generates a video signal based on an image-pickup-device output signal outputted from the image pickup unit 107, and outputs the video signal to the image display unit 121. Specifically, in the present embodiment, an optical image (endoscope image) picked up by the image pickup unit 107 is displayed as a video on the image display unit 121.

Note that the endoscope 101 does not necessarily need to be connected to the external device 120 or the image display unit 121 but may include, for example, part or entire of the image processing unit or the monitor.

A light guide (not illustrated in the drawing) to be described later as the optical fiber bundle is configured to transmit light emitted from the light source unit of the external device 120 to an illumination window as an illumination light emission portion of the distal end portion 110. The light source unit may be disposed at the operation portion 103 or the distal end portion 110 of the endoscope 101.

At the operation portion 103, operation buttons 10 such as air feeding and water feeding buttons and a suction button, and the push button unit 1 as a plurality of push button devices for the endoscope for performing releasing and various operation instructions are provided outside the angle operation knob 106.

The push button unit 1 is an endoscope operation means for performing, for the external device 120, remote operations of a Video tape recorder, a video printer, a video disk, and the like and instructions of image freezing, releasing, metering mode control, size change of an output screen on the monitor, and the like.

Subsequently, each push button unit 1 as a push button device for the endoscope according to the present embodiment will be described below in detail.

As illustrated in FIG. 2, the push button unit 1 mainly includes a rubber cap 21 as a finger placement member having elasticity, a first stem 26 as a first operation rod, a second stem 35 as a second operation rod provided on the same axis (an axis X in the drawing) as the first stem 26 in a non-operational state as an initial state, and a switch unit 30.

The rubber cap 21 is a bottomed tubular body formed of an elastic material such as silicon rubber. A fastening pipe 22 is fixed inside an opening end portion of the rubber cap 21.

The fastening pipe 22 is, for example, screwed to a base 23 fixed to an exterior case 41, the exterior case 41 serving as an exterior member of the operation portion 103 of the endoscope 101, the base 23 serving as an exterior member of the operation portion 103. Accordingly, the rubber cap 21 is fixed watertight to the exterior case 41 of the operation portion 103 with the opening end portion in a state being sandwiched between the fastening pipe 22 and the base 23.

The rubber cap 21 includes a non-elastic material 24 and a stem connection portion 25 at an upper part of inside the rubber cap 21, the non-elastic material 24 being formed of metal, hard resin, or the like in a substantially hat shape and serving as an operation member, the stem connection portion 25 being formed of an elastic or hard member and disposed inside the non-elastic material 24 and serving as an operation member.

The first stem 26 includes a lower end portion 27 in an outward flange shape. The first stem 26 is connected to the rubber cap 21 with an upper end part being inserted into the stem connection portion 25 of the rubber cap 21. Specifically, the first stem 26 is inserted and fitted into the stem connection portion 25 with an outer peripheral surface of the upper end part being in substantially planar contact with an inner peripheral surface 25a of the stem connection portion 25.

An end face 25b of the stem connection portion 25 on a lower side is a tapering surface tilted in a radially inward direction to facilitate introduction of the first stem 26, thereby increasing assembly easiness of the first stem 26.

The lower end portion 27 of the first stem 26 is housed in a stem holding pipe 28 as an immobile member in a substantially tubular shape. The first stem 26 protrudes from an upper end of the stem holding pipe 28 and is disposed to be slidable along the axis X passing through a center and swingable at a predetermined angle relative to the axis X.

The stem holding pipe 28 includes an upper end portion 29 in an inward flange shape. The lower end portion 27 of the first stem 26 contacts an inner wall of the upper end portion 29 so that the first stem 26 is disposed not to be removed from the stem holding pipe 28.

The stem holding pipe 28 also includes a lower end portion 28a in an outward flange shape, and the lower end portion 28a is fixed by screwing or the like from a back surface side of the exterior case 41 of the operation portion 103 and is provided so as to protrude inside the rubber cap 21 outside the exterior case 41 and the base 23.

In the stem holding pipe 28, the second stem 35 is housed on the lower side of the first stem 26, is slidable along the axis X passing through the center, and has a predetermined angle relative to the axis X. The second stem 35 includes a lower end portion 36 in an outward flange shape and a convex portion 37 protruding on the lower side from a center of a lower surface of the lower end portion 36.

An upper end surface 35a of the second stem 35 disposed in the stem holding pipe 28 contacts a lower end surface 27a of the lower end portion 27 of the first stem 26, the upper end surface 35a and the lower end surface 27a being in flat plate shapes.

The switch unit 30 is fixed to a lower portion of the stem holding pipe 28 as an immobile member. In the switch unit 30, a switch portion 32 such as a tact switch including an elastic contact point is provided at a lower portion inside a case 31 as an immobile member, and the lower end portion 36 of the second stem 35 is housed above the switch portion 32 in the case 31.

The second stem 35 is disposed to protrude from an upper portion of the switch unit 30 and not to be removed from the case 31 as the lower end portion 36 contacts an inner wall of an upper end portion 38 of the case 31, the upper end portion 38 being in an inward flange shape. The convex portion 37 of the second stem 35 contacts the elastic contact point of the switch portion 32.

Note that the second stem 35 is pushed upward by the elastic contact point of the switch portion 32. The first stem 26 is pushed upward by pushing force from the second stem 35.

The switch portion 32 is electrically connected to a lead line 33 extending from the lower portion of the case 31. The lead line 33 is electrically connected to an electric contact portion provided in the endoscope connector 105.

The above-described push button unit 1 has such a configuration that a switching operation to turn on or off the switch portion 32 can be performed in any of a direction from above along the axis X as a longitudinal direction of the first stem 26 and the second stem 35, which is illustrated with arrow F in the drawing, a side direction orthogonal to the axis X, and a downward oblique direction at an angle relative to the axis X.

The following describes a switching operation when the push button unit 1 according to the present embodiment is pushed from side or obliquely.

As illustrated in FIG. 3, in a state in which the push button unit 1 is pushed in a side direction or an oblique direction, the first stem 26 connected to the rubber cap 21 tilts in a pushing direction.

In this state, part of an upper surface of the outward-flange-shaped lower end portion 27 contacts an inner wall surface of the inward-flange-shaped upper end portion 29 of the stem holding pipe 28 as an immobile member. Accordingly, the first stem 26 is inclined to rotate with a point of the contact as a pivot.

As the first stem 26 is inclined and tilted, the second stem 35 with the upper end surface 35a being in planar contact with the lower end surface 27a of the first stem 26 is inclined in cooperation and tilted in the pushing direction.

Accordingly, the convex portion 37 protruding from a lower end of the second stem 35 is displaced to the lower side and pushes the elastic contact point of the switch portion 32, thereby performing a switching operation to turn on or off the switch portion 32.

In this state, the first stem 26 of the push button unit 1 is fitted with no play in substantially planar contact with the inner peripheral surface 25a of the stem connection portion 25 provided at the rubber cap 21, and moves in conjunction with motion of the rubber cap 21 without temporal delay.

Since the first stem 26 of the push button unit 1 moves in conjunction with the motion of the rubber cap 21 without temporal delay, an amount of pushing of the rubber cap 21 by a user decreases, which improves responsiveness of the switching operation. Accordingly, the push button unit 1 provides improved sensitivity of the switching operation.

The responsiveness of the switching operation, depending on a tilt angle, a length, and the like of the first stem 26 will be described based on a state in which the first stem 26 and the second stem 35 of the push button unit 1 are tilted.

The push button unit 1 can provide improved responsiveness of the switching operation in a case in which the switch portion 32 can be actuated with a small amount of pushing of the rubber cap 21 when the rubber cap 21 is pushed from side or obliquely.

A value ($P/L = \sin \theta$) obtained by dividing a pushing amount P of pushing of the rubber cap 21 in a direction orthogonal to the axis X by a length L of the first stem 26 up to the lower end portion 27 is constant when a tilt angle $\theta$ is defined as an inclination angle for actuating the switch portion 32 with respect to the axis X as a central axis of the first stem 26 standing straight in the initial state as illustrated in FIG. 4.

Thus, in order to reduce the pushing amount P of the rubber cap 21 without changing the tilt angle $\theta$ of the first stem 26, the length L of the first stem 26 up to the lower end portion 27 needs to be reduced.

Note that the length L of the first stem 26 up to the lower end portion 27 is a length of the first stem 26 in an axial direction except for a thickness of the lower end portion 27. The length L of the first stem 26 is set to be shorter than a length of the second stem 35 in a longitudinal axial direction.

Accordingly, in the push button unit 1, the length L of the first stem 26 is shortened so that a position at which the lower end portion 27 of the first stem 26 and the upper end portion 29 of the stem holding pipe 28 as an immobile member contact each other is inside the rubber cap 21 at least outside the base 23 and the exterior case 41 serving as an exterior of the operation portion 103.

Moreover, a value ($D/d = \sin \theta$) obtained by dividing a pushing amount D of pushing of the switch portion 32 by a diameter d of the lower end portion 27 of the first stem 26 is constant as well.

Thus, in order to increase the pushing amount D of the switch portion 32 without changing the tilt angle $\theta$ of the first stem 26, the diameter d of the lower end portion 27 of the first stem 26 needs to be increased.

Accordingly, the push button unit 1 provides improved responsiveness of the switching operation so that the switch portion can be actuated by small motion of the rubber cap 21 as a finger placement member. Moreover, the push button unit 1 can provide improved responsiveness of the switching operation by increasing the diameter d of the lower end portion 27 of the first stem 26.

As described above, the push button unit 1 as a push button device for an endoscope can have a configuration with which the switching operation having favorable responsiveness can be performed with a small amount of pushing of the rubber cap 21 as a finger placement portion.

First Modification

Figure 5:
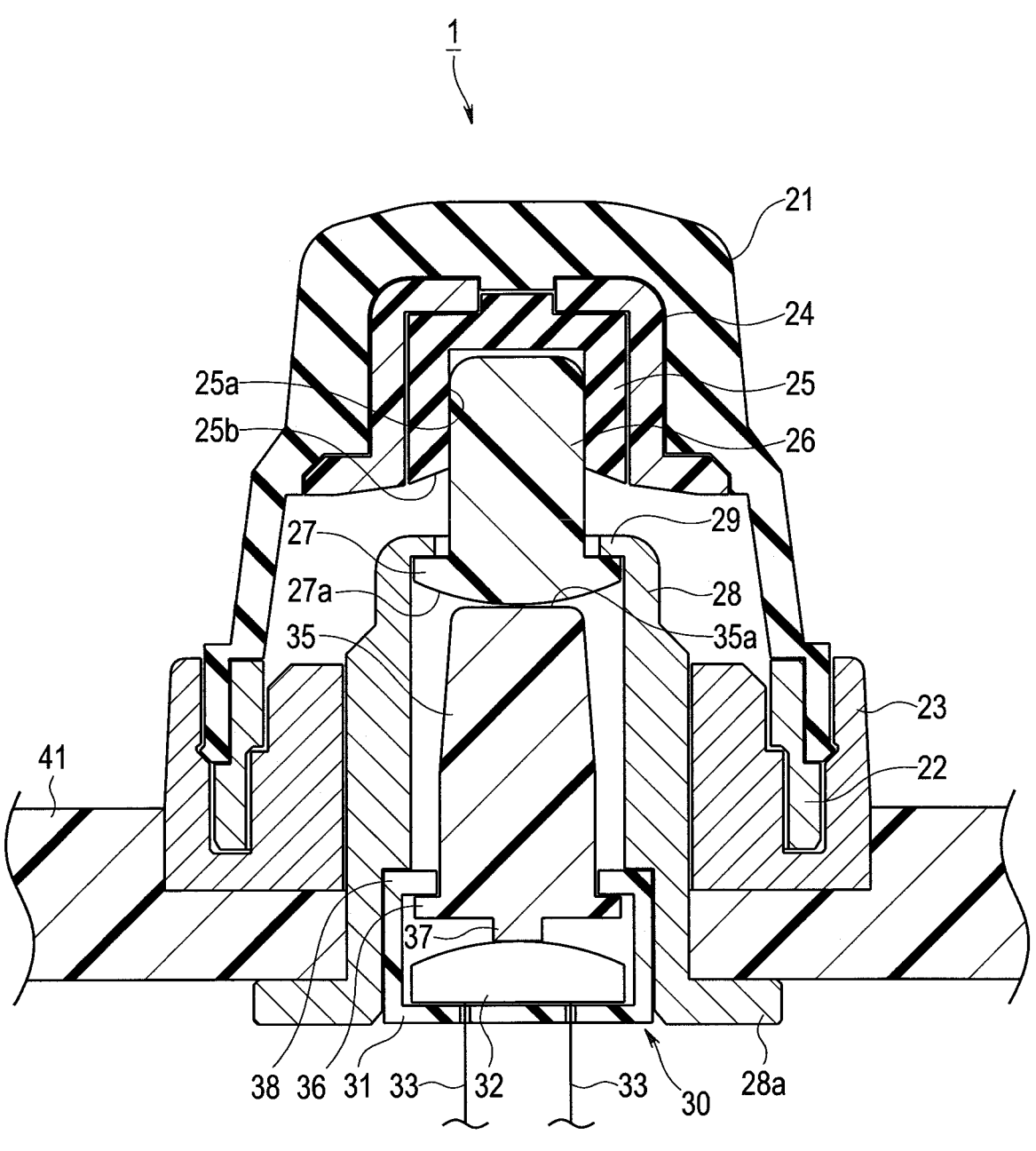
FIG. 5 is a cross-sectional view illustrating a configuration of the push button unit according to a first modification.

FIG. 5 is a cross-sectional view illustrating the configuration of the push button unit according to a first modification.

As illustrated in FIG. 5, the lower end surface 27a of the outward-flange-shaped lower end portion 27 of the first stem 26 may have a convex spherical shape instead of a flat plate shape.

Second Modification

Figure 6:
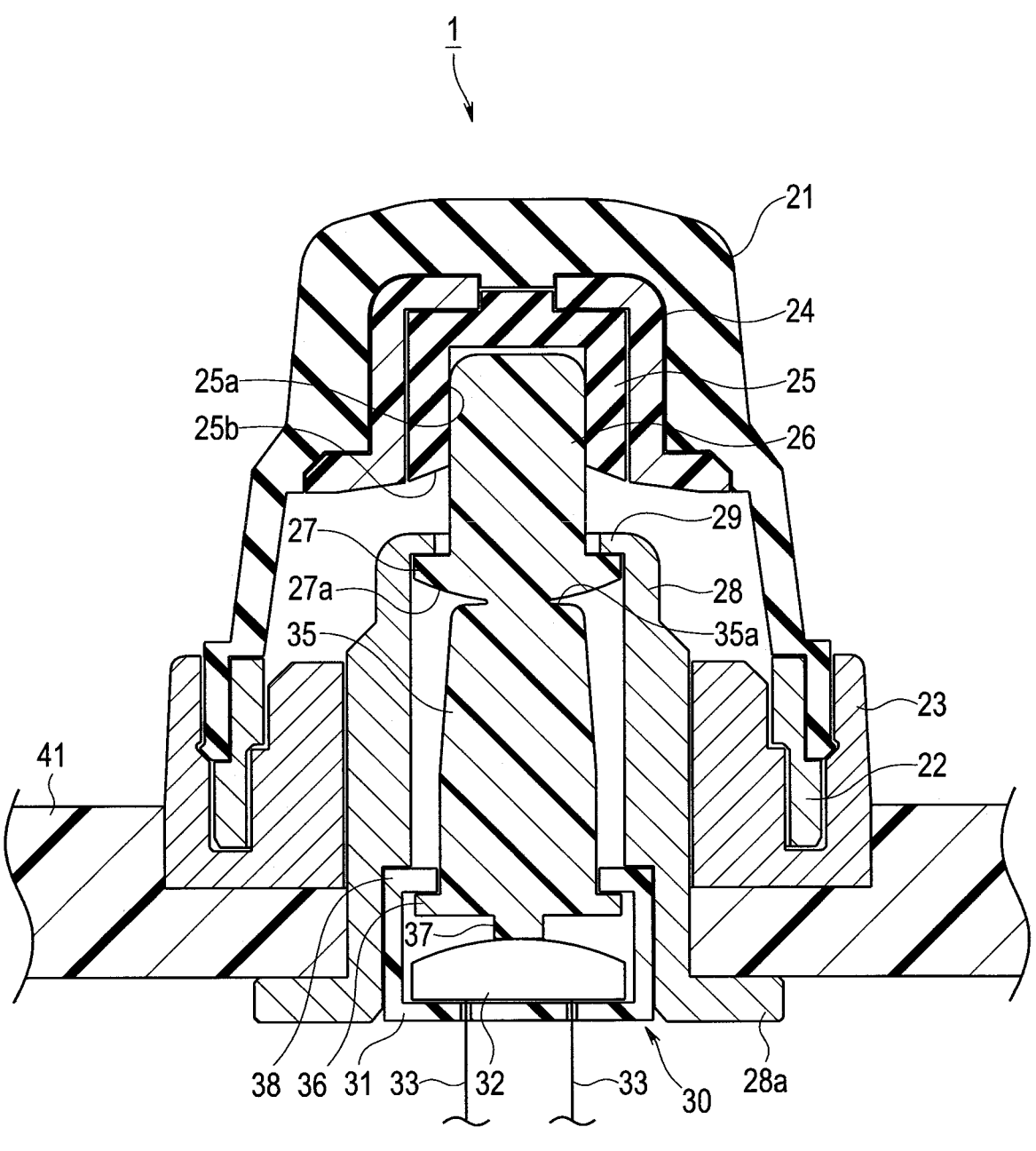
FIG. 6 is a cross-sectional view illustrating a configuration of the push button unit according to a second modification.

FIG. 6 is a cross-sectional view illustrating the configuration of the push button unit according to a second modification.

As illustrated in FIG. 6, the first stem 26 and the second stem 35 may be integrally formed. With such a configuration, as well, similarly to the above description of the embodiment, the push button unit 1 as a push button device for an endoscope can have a configuration with which the switching operation having favorable responsiveness can be performed with a small amount of pushing of the rubber cap 21 as a finger placement portion.

The invention described above in each of the embodiments is not limited to the embodiment and the modifications but may include various kinds of other modifications without departing from the gist of the invention when performed. Moreover, inventions at various kinds of stages are included in the above-described embodiment, and various kinds of inventions can be extracted with appropriate combinations among a plurality of disclosed components.

For example, some components may be deleted from among all components described in the embodiment, and a configuration from which the components are deleted may be extracted as an invention as long as a described problem can be solved and described effects can be obtained.

According to the present invention, it is possible to provide a small-sized push button mechanism for an endoscope in which size increase of an operation portion is prevented.

What is claimed is:

1. A push button device for an endoscope, the push button device comprising:

a finger placement member having elasticity and disposed at an operation portion of the endoscope;

a connection member having a concavity provided at a first central portion of the finger placement member;

a first stem that has a protrusion at a second central portion of an upper end portion of the first stem, the protrusion being inserted into the concavity of the connection member, the first stem being disposed so as to be slidable along a longitudinal axis and swingable relative to the longitudinal axis;

a second stem provided so as to be slidable along the longitudinal axis and swingable relative to the longitudinal axis, and the second stem configured to move in conjunction with motion of the first stem with an upper central end surface of the second stem being in contact with a lowest central end surface of the first stem in a longitudinal axis direction;

a fixed member fixed relative to the first and second stems, the fixed member having a cavity for slidably and swingably holding the first stem and the second stem; and a switch configured to be switched by displacement of the second stem moving in conjunction with the motion of the first stem when the finger placement member is pushed;

wherein the lowest central end surface of the first stem and the upper central end surface of the second stem are each planar surfaces;

the first stem is inserted into the cavity of the fixed member, the cavity has an inner diameter larger than a corresponding outer diameter of the first stem such that a central axis of the first stem rotates relative to the longitudinal axis when the finger placement member is pushed in an oblique direction relative to the longitudinal axis direction; and the lowest central end surface of the first stem maintains planar contact with the upper central end surface of the second stem when the finger placement member is pushed in the oblique direction and the first stem rotates relative to the longitudinal axis.

2. The push button device for the endoscope according to claim 1, wherein lengths of the first stem and the second stem in the longitudinal axis are set so that a position at which the lower end surface of the first stem and the upper end surface of the second stem contact each other is outside a surface of an exterior member of the operation portion.

3. The push button device for the endoscope according to claim 2, wherein the length of the first stem is shorter than the length of the second stem in the longitudinal axis.

4. The push button device for the endoscope according to claim 1, wherein the fixed member is formed in a tubular shape for holding the first stem and the second stem on a same axis.

5. The push button device for the endoscope according to claim 4, wherein the fixed member protrudes inside the finger placement member outside an exterior member of the operation portion.

6. The push button device for the endoscope according to claim 5, wherein the switch includes an elastic contact point that pushes the second stem so that the first stem protrudes from an upper portion of the fixed member.

7. The push button device for the endoscope according to claim 6, wherein the first stem and the second stem include outward flanges at lower end portions, and the fixed member includes an inward flange that contacts the outward flanges.

8. The push button device for the endoscope according to claim 1, wherein a tapering surface tilted in a radially inward direction is formed at an opened side end face of the connection member.

9. An endoscope comprising:

an operation portion grasped by a user;

a finger placement member having elasticity and disposed at the operation portion;

a connection member having a concavity provided at a first central portion of the finger placement member;

a first stem that has a protrusion at a second central portion of an upper end portion of the first stem, the protrusion being inserted into the concavity of the connection member, the first stem being disposed so as to be slidable along a longitudinal axis and swingable relative to the longitudinal axis;

a second stem provided so as to be slidable along the longitudinal axis and swingable relative to the longitudinal axis, and the second stem configured to move in conjunction with motion of the first stem with an upper central end surface of the second stem being in contact with a lowest central end surface of the first stem in a longitudinal axis direction;

a fixed member fixed relative to the first and second stems, the fixed member having a cavity for slidably and swingably holding the first stem and the second stem;

a switch configured to be switched by displacement of the second stem moving in conjunction with the motion of the first stem when the finger placement member is pushed;

wherein the lowest central end surface of the first stem and the upper central end surface of the second stem are each planar surfaces;

the first stem is inserted into the cavity of the fixed member, the cavity has an inner diameter larger than a corresponding outer diameter of the first stem such that a central axis of the first stem rotates relative to the longitudinal axis when the finger placement member is pushed in an oblique direction relative to the longitudinal axis direction; and the lowest central end surface of the first stem maintains planar contact with the upper central end surface of the second stem when the finger placement member is pushed in the oblique direction and the first stem rotates relative to the longitudinal axis.

10. The push button device for the endoscope according to claim 1, wherein the lowest central end surface of the first stem and the upper central end surface of the second stem slide relative to each other when the central axis of the first stem rotates relative to the longitudinal axis.

11. The endoscope according to claim 9, wherein the lowest central end surface of the first stem and the upper central end surface of the second stem slide relative to each other when the central axis of the first stem rotates relative to the longitudinal axis.

12. The push button device for the endoscope according to claim 1, wherein no portions of the first stem and the second stem overlap in the longitudinal axis direction.

13. The endoscope according to claim 9, wherein no portions of the first stem and the second stem overlap in the longitudinal axis direction.

14. The push button device for the endoscope according to claim 1, wherein
the first stem includes an outward flange at a lower end portion,
the fixed member includes an inward flange that contacts the outward flange; and
an inner diameter of the inward flange of the fixed member is smaller than an outer diameter of the outward flange of the first stem.

15. The push button device for the endoscope according to claim 1, wherein
the first stem includes an outward flange at a lower end portion,
the fixed member includes an inward flange that contacts the outward flange; and
an inner diameter of the inward flange of the fixed member is larger than an outer diameter of portions of the first stem other than the outward flange.

16. The push button device for the endoscope according to claim 1, wherein
an outer diameter of a lowermost planar surface of the first stem in a direction orthogonal to the longitudinal axis direction is larger than an outer diameter of an uppermost planar surface of the second stem in the direction orthogonal to the longitudinal axis direction.

17. The push button device for the endoscope according to claim 1, wherein an overall length of the first stem in the longitudinal axis direction is shorter than an overall length of the second stem in the longitudinal axis direction.

18. The push button device for the endoscope according to claim 1, wherein the first stem and the second stem rotate together relative to the longitudinal axis while maintaining the planar contact between the lowest central end surface of the first stem and the upper central end surface of the second stem.

19. The push button device for the endoscope according to claim 9, wherein the first stem and the second stem rotate together relative to the longitudinal axis while maintaining the planar contact between the lowest central end surface of the first stem and the upper central end surface of the second stem.

* * * * *